(12) United States Patent
Chevalier

(10) Patent No.: US 6,277,388 B1
(45) Date of Patent: Aug. 21, 2001

(54) STABLE GELLED AQUEOUS COMPOSITION WITH A HIGH ELECTROLYTE CONTENT

(75) Inventor: Veronique Chevalier, Villecresnes (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/405,232

(22) Filed: Sep. 24, 1999

(30) Foreign Application Priority Data

Sep. 25, 1998 (FR) .................................................. 99 12041

(51) Int. Cl.[7] ................. A61K 6/00; A61K 7/00; A61K 7/02; A61K 7/06; C08L 33/14
(52) U.S. Cl. ................. 424/401; 424/400; 424/486; 424/677; 424/70.11; 424/78.01; 424/78.03; 524/832; 524/505
(58) Field of Search ..................... 424/401, 400, 424/677, 486, 70.11, 78.03, 78.01; 524/832, 505; 260/29.6

(56) References Cited

U.S. PATENT DOCUMENTS

| | | | |
|---|---|---|---|
| 4,079,028 | * 3/1978 | Emmons et al. | 260/29.6 |
| 4,180,491 | 12/1979 | Kim et al. | |
| 5,650,159 | * 7/1997 | Lion et al. | 424/401 |
| 5,951,991 | * 9/1999 | Wagner et al. | 424/401 |
| 6,013,270 | * 1/2000 | Hargraves et al. | 424/401 |
| 6,107,398 | * 8/2000 | Mallo et al. | 524/832 |
| 6,136,328 | * 10/2000 | Sebillotte-Arnaud et al. | 424/401 |

FOREIGN PATENT DOCUMENTS

| | | |
|---|---|---|
| 0 687 462 A1 | 12/1995 | (EP) . |
| 0 705 594 A1 | 4/1996 | (EP) . |
| 0 795 320 A1 | 9/1997 | (EP) . |
| WO 96/19184 | 6/1996 | (WO) . |
| WO 97/21743 | 6/1997 | (WO) . |

OTHER PUBLICATIONS

Mineral Waters of France and its Wintering Stations. By A. Vintras, M.D. , J. & A. Churchill, London, 1883 (Book).*
Derwent Publications Ltd., london, GB; AN 96–272719 XP002109097 (Abstract Only).
WO 96/19184, Jun. 27, 1996 (Corrected Version).

* cited by examiner

Primary Examiner—Diana Dudash
Assistant Examiner—Mina Haghighatian
(74) Attorney, Agent, or Firm—Oblon, Spivak, McClelland, Maier & Neustadt, P.C.

(57) ABSTRACT

Compositions suitable for cosmetic and/or dermatological use which contain at least one electrolyte and/or at least one primary alcohol, at least one associative polyurethane, at least one oxyalkylenated polymer, and water.

22 Claims, No Drawings

STABLE GELLED AQUEOUS COMPOSITION WITH A HIGH ELECTROLYTE CONTENT

BACKGROUND OF THE INVENTION

1. Field of the Invention

The present invention relates to a stable gelled composition, in particular a topical composition, which contains a large amount of electrolyte or a primary alcohol and to its use, treatment, protection and/or care of the skin, scalp, mucous membranes, nails and/or hair.

2. Discussion of the Background

Gelling agents are frequently used for topical application in the cosmetic, dermatological and pharmaceutical fields in the form of gels or emulsions for improving the consistency of the composition. The majority of gelling agents conventionally used are aqueous gelling agents and in particular carboxyvinyl polymers, which are neutralized with a base. However, some compounds cannot be used in these compositions because they are incompatible with gelling agents. For example, electrolytes, e.g., inorganic and organic salt, are incompatible with carboxyvinyl polymer gelling agents because they "break down" and liquify emulsions gelled with carboxyvinyl polymers. Thus, compositions containing carboxyvinyl polymers and electrolytes are often devoid of a good consistency.

Electrolytes are particularly desirable components of thickened, topical gel compositions where they have a beneficial effect on the skin or hair and are used in combination with cosmetic, dermatological, and/or pharmaceutical active agents.

Polysaccharide-type gelling agents, such as guar gums, xanthan gums and cellulose derivatives, have been used in place of carboxyvinyl polymers. EP-A-654270 describes a topical composition intended for the treatment of acne and seborrhoeic dermatitis containing a mixture of salts and hydroxyethyl cellulose as the gelling agent. However, these compositions, especially aqueous gels containing no oily phase, have an unsightly lumpy appearance. In addition, they leave the skin "wet looking" after application because these compositions do not penetrate sufficiently into the skin. Therefore, these materials have limited use as cosmetic and/or dermatological agents, where product appearance is critical. The combination of these cellulose derivatives with another thickening agent, such as silicate as described in WO-A-93/8230, provides compositions with the same disadvantages.

Furthermore, the incorporation of primary alcohol and in particular of ethanol into gelled compositions result in the same problems of stability. It is important to be able to use gelled compositions comprising a primary alcohol because the primary alcohol is often needed as solvent for solubilization of active agents.

Therefore, the need remains for gel compositions which overcome the disadvantages of known gelling agents: lack of consistency, instability, lumpy appearance, unpleasant sensation to the touch and incompatibility with electrolytes.

The present inventor has now unexpectedly found a class of associative polymers, in combination with an oxyalkylenated polymer, that stabilize compositions containing a high content of electrolyte and/or of primary alcohol.

SUMMARY OF THE INVENTION

An object of the present invention is to provide a stable gelled composition containing a cosmetic, dermatological, and/or pharmaceutical active agent and electrolyte which is useful for the treatment, protection and/or care of the skin, mucous membranes, scalp, nails, and hair.

Another object of the present invention is to provide a stable gelled composition containing a large quantity of electrolyte.

Another object of the invention is to provide a method of treating, protecting, and/or caring for the skin, mucous membranes, scalp, nails, and hair.

These objects and others may be accomplished with a composition containing at least one electrolyte and/or at least one primary alcohol, at least one associative polyurethane, at least one oxyalkylentated polymer, and water.

The above objects may also be accomplished by a method of treating, protecting, and/or caring for the skin, mucous membranes, scalp, nails, and hair of a subject, where the composition contains at least one cosmetic, dermatological, and/or pharmaceutical active agent, at least one electrolyte and/or at least one primary alcohol, at least one associative polyurethane, at least one oxyalkylentated polymer, and water.

The above objects may also be accomplished with a process of manufacturing a composition by combining at least one cosmetic, dermatological, and/or pharmaceutical active agent, at least one electrolyte and/or at least one primary alcohol, at least one associative polyurethane, at least one oxyalkylentated polymer, and water to produce a gel.

DETAILED DESCRIPTION OF THE INVENTION

A more complete appreciation of the invention and many of the attendant advantages thereof will be readily obtained as the same becomes better understood by reference to the following detailed description.

The present composition can be used in all areas where it is desired to obtain a thickened composition in the presence of electrolytes and/or alcohol. In particular, the present composition may be used in the cosmetic, dermatological and pharmaceutical fields. The present invention is directed to a composition for topical care, protection or treatment. The composition must comprise a topically acceptable medium, that is to say compatible with the skin, mucous membranes, nails, scalp and/or hair. It can be provided in any pharmaceutical dosage form appropriate for topical application and in particular in the form of a water-in-oil (W/O), oil-in-water (O/W), triple (W/O/W) or (O/W/O) dispersion or emulsion. The composition according to the invention may also contain ionic and/or nonionic lipid vesicles. The composition can constitute, for example, a cream or an ointment. The amounts of the various constituents of the composition are those conventionally used in the cosmetic, dermatological and/or pharmaceutical fields.

The present composition may have any viscosity ranging from 0.1 to 50 Pa·s (1 to 500 poises) and preferably from 0.5 to 10 Pa·s (5 to 100 poises). The viscosity is measured with a Rhéomat 180 viscometer at 25° C., at a shear rate of 200 s$^{-1}$.

The associative polyurethanes are nonionic sequential copolymers containing in a chain, both hydrophilic sequences of generally polyoxyethylenated nature and hydrophobic sequences which can be aliphatic linkages alone, cycloaliphatic and/or aromatic liikages.

Preferably, these polymers contain at least two alkyl chains having from 6 to 30 carbon atoms, separated by a hydrophilic sequence. The alkyl chains may be pendant chains or chains at the end of the hydrophilic sequence. Preferably, the polymers may contain one or more pendant chains and alkyl chain at one end or at both ends of a hydrophilic sequence. The polymers can be sequential in triblock or multiblock form. The hydrophobic sequences can therefore be at each end of the chain, e.g., triblock copolymer with a hydrophilic central sequence, or distributed both at the ends and in the chain, e.g., multisequential copolymer. The polymers can also be grafted polymers or star polymers. Preferably, the polymers are triblock copolymers, the hydrophilic sequence of which is a polyoxyethylenated chain containing from 50 to 1000 oxyethylenated groups.

Associative polyurethanes generally contain a urethane bond between the hydrophilic sequences. Therefore, associative polyurethanes also include polymers, the hydrophilic sequences of which are bonded via other chemical bonds to the lipophilic sequences. Particularly preferred and commercially available sources of associative polyurethanes are the $C_{16}$—$OE_{120}$—$C_{16}$ polymer available from Hüls under the name Sérad FX1100 (molecule with urethane functional group and average molecular weight of 1300, OE being an oxyethylenated unit), Rhéolate 205 with a urea functional group, Rheolate 208, or Rhéolate 204 available from Rheox.

The polymers may be in solutions or dispersions, in particular in water or in an aqueous/alcoholic medium. Preferred and commercially available polymers in solution or dispersions are Sérad FX1010 (available from Hüls), Sérad 1035 (available from Hüls), Rhéolate 255 (available from Rheox), Rhéolate 278 (available from Rheox) and Rhéolate 244 (available from Rheox). Other commercially available polymers are DW 1206F, DW 1206J, DW 1206B, Acrysol RM 184, Acrysol 44, and Acrysol 46, available from Röhm & Haas. Preferably, Acrysol 46 solution containing an active material content of 15% is present in the composition.

The present composition contains one or more associative polyurethanes in an amount sufficient to ensure the stability of the gelled composition. The associative polyurethanes may be present in the composition in any quantity ranging from 0.1 to 40%, preferably from 0.5 to 20% by weight of active material based on the total weight of the composition. These ranges include all specific values and subranges there between, including 0.75, 2, 3.5, 8, 10, 20, 25, and 35% by weight.

The oxyalkylenated polymer includes polyethylene glycols, polypropylene glycols, derivatives of fatty acids, glycerylated derivatives of polyethylene glycol, glycerylated derivatives of polypropylene glycol. The oxyalkylenated polymer may include polymers containing from 2 to 100 and preferably from 4 to 80 oxyethylenated and/or oxypropylenated groups, and their derivatives. These ranges include all specific values and subranges there between, including 5, 10, 20, 30, 40, 50, 60, and 70 oxyethylenated and/or oxypropylenated groups.

The term fatty acid includes acids having an alkyl chain containing from 8 to 30 carbon atoms. The present composition may contain one or more oxyalkylenated polymers. Preferred oxyalkylenated polymers include polyethylene glycols, polypropylene glycols, PEG-20, PEG-32, PPG-15, fatty acid derivatives of polyethylene glycols, fatty acid derivatives polypropylene glycols, polyethylene glycol stearates, polyethylene glycol oleates, polyethylene laurates, polypropylene glycol stearates, polypropylene glycol oleates, polypropylene glycol laurates, glycerated derivatives of fatty acids, glycerated derivatives of polyethylene glycol, glycerated derivatives of polypropylene glycol, and glycerated derivatives of PEG-30 glyceryl stearate. Preferably, oxyalkylenated polymers are polyethylene glycol stearate with 50 oxyethylenated groups (PEG-50 stearate), polypropylene glycol ether of stearyl alcohol with 15 oxypropylenated groups (PPG-15 stearyl ether). The oxyalkylenated polymer may be present in the composition in any quantity ranging from 0.1 to 10%, preferably from I to 5% by weight based on the total weight of the composition. These ranges include all specific values and subranges there between, including 0.5, 0.75, 2, 4, 6, and 8% by weight.

The term primary alcohols includes alcohols which have only one hydroxyl group. The present composition may contain any aliphatic alcohol with a linear or branched chain comprising from 1 to 6 carbon atoms, preferably from 2 to 4 carbon atoms. Preferred primary alcohols are ethanol, propanol, isopropanol, and mixtures thereof.

The quantity of primary alcohol will vary dependent on the expected purpose for the composition and the amount of active agent, if the active agent is to be dissolved in the alcohol. The primary alcohol or alcohols may be present in the composition in any quantity ranging from 1 to 20%, preferably from 1 to 15% by weight based on the total weight of the composition. These ranges include all specific values and subranges there between, including 3,6, 9, 12, and 17% by weight.

The term electrolyte includes inorganic salts. Preferred electrolytes are salts of monovalent, divalent or trivalent metal ions. More preferred electrolytes are salts of alkaline earth metals (beryllium, magnesium, calcium, strontium and barium), salts of alkali metals (such as lithium, sodium and potassium) or salts of yttrium, lanthanum, cerium, praseodymium, neodymium, promethium, samarium, europium, gadolinium, terbium, dysprosium, holmium, erbium, thulium, ytterbium, lutetium, tin, zinc, manganese, cobalt, nickel, iron, copper, rubidium, aluminum, silicon, selenium, and mixtures thereof.

The anions of these salts may be carbonates, bicarbonates, sulfates, glycerophosphates, borates, chlorides, nitrates, acetates, hydroxides, persulfates, α-hydroxy acid carboxylates (such as citrates, tartrates, lactates, malates), fruit acid carboxylates or carboxylates of amino acids (such as aspartate, arginate, glycocholate and fumarate).

Preferably, the electrolytes are calcium salts, magnesium salts, sodium salts, potassium salts. These electrolyte include calcium nitrate, magnesium nitrate, strontium nitrate, calcium borate, magnesium borate, calcium chloride, sodium chloride, magnesium chloride, potassium chloride, strontium chloride, neodymium chloride, manganese chloride, sodium chloride magnesium sulphate, calcium sulphate, calcium acetate, magnesium acetate, magnesium bromide and their mixtures.

A preferred mixture is a "mixture of Dead Sea salts" where the main salts present in the Dead Sea are in an aqueous mixture containing 30 to 35% of magnesium chloride, 20 to 28% of potassium chloride, 3 to 10% of sodium chloride, 0.2 to 1% of calcium chloride, 0.1 to 0.6% of magnesium bromide and 0.1 to 0.5% of insolubles.

Another preferred mixture of electrolytes are found in thermal or mineral water which contain dissolved minerals and trace elements. In general, a mineral water is fit for consumption, whereas this is not always true of thermal water.

Preferred thermal or mineral water include water from Vittel, water from the Vichy basin, water from Uriage, water from La Roche Posay, water from La Bourboule, water from Enghien-les-Bains, water from Saint-Gervais-les-Bains, water from Neris-les-Bains, water from Allevard-lesBains, water from Digne, water from Maiziéres, water from Neyrac-les-Bains, water from Lons-le-Saunier, water; from Eaux-Bonnes, water from Rochefort, water from Saint Christau, water from Fumades, water from Avéne and water from Tercis-les-Bains.

The electrolyte may be present in the composition in any quantity ranging from 0.5 to 40%, preferably from 5 to 20% by weight, based on the total weight of the composition. These ranges include all specific values and subranges there between, including 0.75, 1.5, 8, 12, 19, 26, 30, and 37% by weight.

When the composition of the invention is an emulsion or a dispersion, the proportion of the fatty phase can range from 5 to 80%, preferably from 5 to 50% by weight based on the total weight of the composition. The oils, the emulsifiers and optionally the coemulsifiers used in the composition include those conventionally used in the cosmetic, dermatologic, and pharmaceutical fields. Preferred emulsifiers include the oxyalkylenated polymers described above, esters of fatty acids, esters of polyethylene glycol, esters of polypropylene glycol and esters of glycerol (glycerol stearate). Other emulsifiers that may be used in the present composition are disclosed in Kirk-Othmer Encyclopedia of Chemical Technology, Volume 7, Fourth Edition, 1993, pages 572–619.

The emulsifier and the optional coemulsifier are generally present in the composition ranging from 0.3 to 30%, preferably from 0.5 to 20% by weight based on the total weight of the composition. These ranges include all specific values and subranges there between, including 0.75, 3, 6, 9, 13, 21, and 28% by weight.

Preferable oils include oils of vegetable origin (groundnut oil), oils of animal origin, synthetic oils (such as fatty esters, e.g., isopropyl myristate), silicone oils, fluorinated oils, mineral oils, fatty substances, fatty alcohols, fatty acids, waxy compounds, waxes, and mixtures thereof. Oils and other fatty substances which may be used in the present composition are disclosed in Kirk-Otlmier Encyclopedia of Chemical Technology, Volume 7, Fourth Edition, 1993, pages 572–619 incorporated herein by reference.

The present composition may also contain adjuvants which are well-known to those of ordinary skill in the cosmetic, pharmaceutical and/or dermatological fields. Preferable adjuvants include active agents, preservatives, antioxidants, complexing agents, solvents, fragrances, fillers, sunscreen agents, bactericides, odor absorbers and coloring materials. Other examples of adjuvants are disclosed in Kirk-Othmer Encyclopedia of Chemical Technology, Volume 7, Fourth Edition, 1993, pages 572–619 incorporated herein by reference.

These adjuvants, depending on their nature, can be introduced into the fatty phase, into the aqueous phase and/or into lipid vesicles. The amount of adjuvant in the composition may vary widely. Preferably, the composition contains from 0.01 to 20% by weight of adjuvant. These ranges include all specific values and subranges there between, including 0.1, 0.5, 1, 4, 7, 13, and 17% by weight.

The term active agent includes any substance having a cosmetic or dermatological effect when applied to the skin, scalp, hair, mucous membranes or nails. Active agents include moisturizers(such as polyols and glycerol), active agents for treating the signs of ageing, acne, dermatitides, pigmental blemishes, vitamins (such as vitamin C (ascorbic acid), vitamin E (tocopherol), vitamin A (retinal), their esters, and other derivatives), betahydroxy acids (such as salicylic acid and its derivatives, e.g., 5-(n-octanoyl) salicylic acid), alpha-hydroxy acids (such as lactic acid and glycolic acid), retinoic acid, retinoic acid derivatives, and whitening active agents (such as kojic acid and caffeic acid).

The present composition is prepared using procedures well-known to those of ordinary skill in the art. When the composition contains only an aqueous phase, the components may be mixed and stirred until a homogeneous mixture is obtained. Heat may used if desired. When the composition contains hydrophobic components, the aqueous phase and hydrophobic components may be prepared separately and then mixed together. The aqueous and hydrophobic components may also be mixed at the same time.

Having generally described this invention, a further understanding can be obtained by reference to certain specific examples which are provided herein for purposes of illustration only, and are not intended to be limiting unless otherwise specified.

EXAMPLES

The amounts given are as % by weight.

Example 1

Oil-in-water Emulsion

| Oily phase: | |
|---|---|
| Cetyl alcohol | 5% |
| Glyceryl stearate | 2% |
| PEG-50 stearate | 2% |
| Groundnut oil | 6.2% |
| Isopropyl myristate | 3% |
| Aqueous phase: | |
| Strontium chloride | 7% |
| Acrysol 46 (comprising 15' of active material) | 6.7% (i.e., 1% of active material) |
| Demineralized water | q.s. for 100% |

The cream obtained remains stable after two months at 45° C. It was effective for use as a night cream.

Example 2

Oil-in-water Emulsion

| Oily phase: | |
|---|---|
| Cetyl alcohol | 5% |
| Glyceryl stearate | 2% |
| PEG-50 stearate | 2% |
| Groundnut oil | 6.2% |
| Isopropyl myristate | 3% |
| Aqueous phase: | |
| Ethanol | 7% |
| 5-(n-Octanoyl)salicylic acid | 0.5% |
| Acrysol 46 (comprising 15% of active material) | 6.7% (i.e., 1% of active material) |
| Demineralized water | q.s. for 100% |

The cream obtained remains stable after two months at 45° C. It was effective for use as a day cream.

Comparative Example 1

An emulsion identical to that of Example 1 or 2 but not containing Acrysol 46 polymer was prepared. The emulsion obtained did not remain stable after 2 months at 45° C. and separated into two phases.

Comparative Example 2

An emulsion identical to that of Example 1 or 2 but not containing PEG-50 stearate was prepared. The emulsion obtained was not thickened and rapidly broke down, separating into two phases.

Example 3

Oil-in-water Emulsion

| Oily phase: | |
| --- | --- |
| Cetyl alcohol | 5% |
| Glyceryl stearate | 2% |
| PEG-50 stearate | 2% |
| Groundnut oil | 6.2% |
| Isopropyl myristate | 3% |
| Aqueous phase: | |
| Ethanol | 7& |
| Acrysol 46 (comprising 15% of active material) | 6.7% (i.e., 1% of active material) |
| Mixture of Dead Sea salts | 5% |
| Demineralized water | q.s. for 100% |

The cream obtained remains stable after two months at 45° C. It was effective for use as a day cream.

Example 4

Oil-in-water Emulsion Oily phase

| Cetyl alcohol | 5% |
| --- | --- |
| Glyceryl stearate | 2% |
| PPG-15 stearate ether | 2% |
| Groundnut oil | 6.2% |
| Isopropyl myristate | 3% |
| Aqueous phase: | |
| Ethanol | 7% |
| Dead Sea salts | 5% |
| Acrysol 46 (comprising 15% of active material) | 6.7% (i.e., 1% of active material) |
| Demineralized water q.s. for | 100% |

The cream obtained remains stable after two months at 45° C. It was effective for use as a day cream.

Obviously, numerous modifications and variations of the present invention are possible in light of the above teachings. It is therefore to be understood that within the scope of the appended claims, the invention may be practiced otherwise than as specifically described herein.

The priority document of the present application, French Patent No. 9812041 filed Sep. 25, 1998 is hereby incorporated by reference.

What is claimed is:

1. A composition, comprising:
   at least one electrolyte and/or at least one primary alcohol;
   at least one associative polyurethane;
   at least one oxyalkylenated polymer selected from the group consisting of: polyethylene glycols, polypropylene glycols, derivatives of fatty acids, derivatives of polyethylene glycol, derivatives of polypropylene glycol, glycerylated derivatives of fatty acids, glycerylated derivatives of polyethylene glycol, and glycerylated derivatives of polypropylene glycol; and water.

2. The composition of claim 1, wherein the associative polyurethane is a sequential or grafted polymer comprising at least two alkyl chains having from 6 to 30 carbon atoms, separated by a hydrophilic sequence.

3. The composition of claim 1, wherein the associative polyurethane comprises a polyoxyethylenated hydrophilic sequence.

4. The composition of claim 1, wherein the associative polyurethane is a triblock polymer.

5. The composition of claim 1, comprising 0.1 to 40% by weight of the associative polyurethane.

6. The composition of claim 1, wherein the primary alcohol is an aliphatic alcohol with a linear or branched chain comprising from 2 to 4 carbon atoms.

7. The composition of claim 1, wherein the primary alcohol is ethanol or a mixture of ethanol and another primary alcohol.

8. The composition of claim 1, comprising 0.1 to 20% by weight of the primary alcohol.

9. The composition of claim 1, comprising 0.5 to 40% by weight of the electrolyte.

10. The composition of claim 1, wherein the electrolyte is a mono-, di- or trivalent metal salt.

11. The composition of claim 1, wherein the electrolyte comprises a metal ion selected from the group consiting of: barium, calcium, strontium, sodium, potassium, magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminum, silicon, selenium and their mixtures.

12. The composition of claim 1, wherein the electrolyte comprises an anion selected from the group consisting of: chloride, borate, bicarbonate, carbonate, nitrate, hydroxide, sulphate, persulphate, glycerophosphate or acetate ions, ions of α-hydroxy acids, a carboxylate of a fruit acid, a carboxylate of a amino acid, and mixtures thereof.

13. The composition of claim 1, wherein the electrolyte comprises a salt selected from the group consisting of: magnesium chloride, potassium chloride, sodium chloride, calcium chloride, magnesium bromide and their mixtures.

14. The composition of claim 1, wherein the electrolyte comprises an aqueous mixture of a thermal and/or mineral water.

15. The composition of claim 1, wherein the oxyalkylenated polymer comprises from 2 to 100 oxyethylenated and/or oxypropylenated groups, and their derivatives.

16. The composition of claim 1, comprising 0.1 to 10% by weight of the oxyalkylenated polymer.

17. The composition of claim 1, wherein the composition has a viscosity from 0.1 to 50 Pa·s.

18. The composition according to claim 1, wherein the composition is an emulsion.

19. The composition of claim 18, wherein the composition further comprises a cosmetic and/or dermatological active agent.

20. A method of treating, protecting, and/or caring of the skin, mucous membrane, scalp, nails, and/or hair, comprising applying an effective amount of the composition of claim 1 to the skin, mucous membrane, scalp, nails, and/or hair.

21. A process of manufacturing the composition of claim 1, comprising mixing at least one electrolyte and/or at least one primary alcohol, at least one associative polyurethane, at least one oxyalkylenated polymer, and water.

22. A process of manufacturing the gel composition of claim 19, comprising mixing said cosmetic and/or dermatological active agent, at least one electrolyte and/or at least one primary alcohol, at least one associative polyurethane, at least one oxyalkylenated polymer, and water.

* * * * *